(12) United States Patent
Hu et al.

(10) Patent No.: US 7,169,763 B2
(45) Date of Patent: *Jan. 30, 2007

(54) CYTOCHROME P450 3A INHIBITORS AND ENHANCERS

(75) Inventors: Oliver Yoa-Pu Hu, 2F, No. 81, Alley 5, Lane 24, Sec. 3, Ting-Chou Road, Taipei (TW); Cheng-Huei Hsiong, Taipei (TW); Benjamin Pei-Chung Kuo, Taipei (TW); Li-Heng Pao, Taipei (TW)

(73) Assignee: Oliver Yoa-Pu Hu, Taipei (TW)

( * ) Notice: Subject to any disclaimer, the term of this patent is extended or adjusted under 35 U.S.C. 154(b) by 567 days.

This patent is subject to a terminal disclaimer.

(21) Appl. No.: 10/080,043

(22) Filed: Feb. 22, 2002

(65) Prior Publication Data

US 2003/0166584 A1 Sep. 4, 2003

(51) Int. Cl.
*A61K 31/7004* (2006.01)
(52) U.S. Cl. .................................................. 514/27
(58) Field of Classification Search ................ 514/9, 514/506, 11, 544, 456, 457, 27
See application file for complete search history.

(56) References Cited

U.S. PATENT DOCUMENTS

| | | | |
|---|---|---|---|
| 5,229,116 A * | 7/1993 | Edgar et al. ............... | 514/27 |
| 5,478,723 A * | 12/1995 | Parkinson et al. .......... | 435/4 |
| 5,567,592 A * | 10/1996 | Benet et al. ............. | 435/7.21 |
| 5,665,386 A | 9/1997 | Benet et al. | |
| 5,716,928 A | 2/1998 | Benet et al. | |
| 5,916,566 A * | 6/1999 | Benet et al. ............ | 424/195.18 |
| 5,962,522 A | 10/1999 | Wacher et al. | |
| 6,004,927 A | 12/1999 | Benet et al. | |
| 6,028,054 A | 2/2000 | Benet et al. | |
| 6,063,809 A | 5/2000 | Harris | |
| 6,121,234 A | 9/2000 | Benet et al. | |
| 6,160,006 A * | 12/2000 | Edwards et al. ........... | 514/455 |
| 6,180,666 B1 * | 1/2001 | Wacher et al. ............ | 514/544 |
| 6,509,371 B1 * | 1/2003 | He et al. .................. | 514/455 |
| 2002/0128282 A1 * | 9/2002 | Schellens et al. ......... | 514/297 |

OTHER PUBLICATIONS

Yamahara et al., Journal of Ethnopharmacology, (1991) 33(1-2), pp. 31-36 (abstract).*
Yamahara et al., Yakugaku Zasshi (1998), 98(11), 1446-51 (abstract).*
Lei et al., Zhongcaoyao (1982), 13(8), 368-9 (abstract).*
Hikino et al., Shoyakugaku Zasshi (1984), 38(4), 359-60 (abstract).*
Kai S. Lee; Ibutilide, a New Compound with Potent Class III Antiarrhythmic Activity, Activates a Slow Inward Na+ Current in Guinea Pig Ventricular Cells; The Journal of Pharmacology and Experimental Therapeutics, 1992, p. 99-108, vol. 262, No. 1.

Ilya B. Tsyrlov et al.; Isozyme-and species-specific susceptibility of cDNA-expressed CYP1A P-450s to different flavonoids; Biochimica et Biophysica Acta, 1994, p. 325-335, vol. 1205.
Aleksandra Pastrakuljic et al.; Distinction of CYP1A1 and CYP1A2 Activity by Selective Inhibition Using Fluvoxamine and Isosafrole; Biochemical Pharmacology, 1997, p. 531-538, vol. 53.
Henry P. Ciolino et al.; Dietary flavonols quercetin and kaempferol are ligands of the aryl hydrocarbon receptor that affect CYP1A1 transcription differentially; Biochemical Society, 1999, p. 715-722, vol. 340.
Jukka Maenpaa et al.; Differential Inhibition of Coumarin 7-Hydroxylase Activity in Mouse and Human Liver Microsomes; Biochemical Pharmacology, 1993, p. 1035-1042, vol. 45.
R. Edenharder et al.; The inhibition by flavonoids of 2-amino-3-methylimidazo[4,5-f]quinoline metabolic activation to a mutagen: a structure-activity relationship study; Mutation Research, 1997, p. 21-32, vol. 379.
Wen-Shing Chang et al.; Inhibitory Effects of Flavonoids on Xanthine Oxidase; Anticancer Research, 1993, p. 2165-2170, vol. 13.
A. Galijatovic et al.; Extensive metabolism of the flavonoid chrysin by human Caco-2 and Hep G2 cells; Xenobiotica, 1999, p. 1241-1256, vol. 29, No. 12.
Hroshi Yamazaki et al.; Highly sensitive high-performance liquid chromatographic assay for coumarin 7-hydroxylation and 7-ethoxycoumarin O-deethylation by human liver cytochrome P450 enzymes; Journal of Chromatography B, 1999, p. 13-19, vol. 721.
M.T. Obermeier et al.; Effects of bioflavonoids on hepatic P450 activities; Xenobiotica, 1995, p. 575-584, vol. 25.
S.E. Nielsen et al.; In vitro biotransformation of flavonoids by rat liver microsomes; Xenobiotica, 1998, p. 389-401, vol. 28, No. 4.

* cited by examiner

*Primary Examiner*—Phyllis G. Spivack
(74) *Attorney, Agent, or Firm*—Fei-Fei Chao; Andrews Kurth LLP

(57) ABSTRACT

The present invention provides cytochrome P450 3A (CYP3A) inhibitors and enhancers. Examples of the CYP3A inhibitors include free bases or pharmacologically acceptable salts of at least one of the following compounds: α-naphthoflavone, β-naphthoflavone, apigenin, baicalein, β-myrcene, catechin, 3-phenylpropyl acetate, formononetin, gallic acid, hesperetin, hesperidin, isoquercitrin, lauryl alcohol, luteolin, luteolin-7-glycoside, narigin, nordihydroguaiaretic acid, quercitrin, swertiamarin, terpineol, and trans-cinnamaldehyde. Examples of the CYP3A enhancers include free bases or pharmacologically acceptable salts of at least one of the following compounds: apigenin, formononetin, and luteolin-7-glycoside. The CYP3A inhibitors can be used, alone or co-administered with a drug, to improve the drug bioavailability. The CYP3A inhibitors can also be used as chemopreventors to prevent biotransformation of procarcinogenic compounds into carcinogens via CYP3A activity or for treatment of intestinal or hepatic cancer by inhibit the CYP3A activity. The CYP3A enhancers can be used to improve the enzymatic activity of CYP3A so as to improve the biotransformation and degradation of active drugs or the sustrates of CYP3A from the body. The CYP3A inhibitors and enhancers of the present invention are natural substances extracted from herbs and non-toxic.

4 Claims, 2 Drawing Sheets

CYTOCHROME P450 3A INHIBITORS AND ENHANCERS

FIELD OF THE INVENTION

The present invention relates to chemical compounds that have inhibitory or enhancing effects on cytochrome P450 3A (CYP3A). The preferred inhibitors include free bases or pharmacologically acceptable salts of at least one of the following compounds: nordihydroguaiaretic acid, (+)-catechin, lauryl alcohol, gallic acid, hesperetin, hesperidin, trans-cinnamaldehyde, β-myrcene and narigin. The preferred CYP3A enhancers include free bases or pharmacologically acceptable salts of at least one of the following compounds: apigenin, formononetin, and luteolin-7-glycoside. The CYP3A inhibitors are used, alone or co-administered with a drug, to improve the drug bioavailability of the drug. The CYP3A inhibitors are also used as chemopreventors to prevent biotransformation of procarcinogenic compounds into carcinogens via CYP3A activity or for treatment of intestinal or hepatic cancer by inhibit the CYP3A activity. The CYP3A enhancers are used to improve the enzymatic activity of CYP3A so as to increase the biotransformation and degradation of the drugs or CYP3A substrates in vivo.

BACKGROUND OF THE INVENTION

Cytochrome P450 is a heme-containing protein which was discovered by its unusually reduced carbon monoxide difference spectrum that has an absorbance at 450 nm, which is caused by a thiolate anion acting as the fifth ligand to the heme. The most common reaction catalyzed by cytochrome P450 is hydroxylation, often of a lipophilic substrate. Thus, cytochrome P450 proteins are frequently called hydroxylases. However, cytochrome P450 proteins can perform a wide spectrum of reactions including N-oxidation, sulfoxidation, epoxidation, N-, S-, and O-dealkylation, peroxidation, deamination, desulfuration, and dehalogenation.

In bacteria, the P450 proteins are soluble and approximately 400 amino acids long. In eukaryotes, P450 proteins are larger, being about 500 amino acids. In eukaryotes, the proteins are usually membrane bound through an N-terminal hydrophobic peptide and other less well understood contacts. The two locations of P450 in eukaryotes are the endoplasmic reticulum membrane and the mitochondrial inner membrane, which, collectively, are referred to as "microsomes."

There are more than 1500 known P450 sequences which are grouped into families and subfamily. The cytochrome P450 gene superfamily is composed of at least 207 genes that have been named based on the evolutionary relationships of the cytochromes P450. For this nomenclature system, the sequences of all of the cytochrome P450 genes are compared, and those cytochromes P450 that share at least 40% identity are defined as a family (designated by CYP followed by a Roman or Arabic numeral, e.g., CYP3), and further divided into subfamilies (designated by a capital letter, e.g., CYP3A), which are comprised of those forms that are at least 55% related by their deduced amino acid sequences. Finally, the gene for each individual form of cytochrome P450 is assigned an Arabic number (e.g., CYP3A4).

CYP3A isoenzyme is a member of the cytochrome P450 superfamily which constitutes up to 60% of the total human liver microsomal cytochrome P450 and has been found in alimentary passage of stomach and intestines and livers. CYP3A has also been found in kidney epithelial cells, jejunal mucosa, and the lungs. CYP3A is one of the most abundant subfamilies in cytochrome P450 superfamily.

At least five (5) forms of CYPs are found in human CYP3A subfamily, and these forms are responsible for the metabolism of a large number of structurally diverse drugs. In non-induced individuals, CYP3A may constitute 15% of the P450 enzymes in the liver; in enterocytes, members of the CYP3A subfamily constitute greater than 70% of the CYP-containing enzymes.

The first two (2) CYP3A subfamily members identified were CYP3A3 and CYP3A4. These two (2) CYP3As are so closely related that the majority of studies performed to date have not been able to distinguish their contributions, and thus, they are often referred to as CYP3A3/4. The levels of CYP3A3/4 vary in human liver samples.

CYP3A is responsible for metabolism of a large number of drugs including nifedipine, macrofide antibiotics including erythromycin and troleandomycin, cyclosporin, FK506, teffenadine, tamoxifen, lidocaine, midazolam, triazolam, dapsone, diltiazem, lovastatin, quinidine, ethylestradiol, testosterone, and alfentanil. CYP3A3/4 involves in erythromycin N-demethylation, cyclosporine oxidation, nifedipine oxidation, midazolam hydroxylation, testosterone 6.-β.-hydroxylation, and cortisol 6.-β.-hydroxylation. CYP3A has also been shown to be involved in both bioactivation and detoxication pathways for several carcinogens in vitro.

In recent years, CYP3A has been proven to be the responsible for the first-pass effect of drug degradation. Because CYP3A inhibitors inhibit the CYP3A enzymatic activity, they have the capacity of improving the bioavailability of the drugs. In addition, an effective CYP3A inhibitor can bind to CYP3A and thus decrease the clinical interaction between drugs induced by CYP3A. Furthermore, CYP3A has been shown to be responsible for transforming Alfa toxin $B_1$ and Alfa toxin $G_1$ into carcinogen. Thus, CYP3A inhibitors can also serve as chemopreventors.

Because an effective CYP3A inhibitor has the capability of improving the bioavailability for drugs, decreasing certain clinical drug interactions induced by CYP3A, and acting as a chemopreventor, an effective CYP3A inhibitor is well sought after in the field of medical science.

So far, there have been reports relating to the improvement of drug bioavailability. For example, U.S. Pat. Nos. 5,716,928, 5,665,386, 5,916,566, and 6,121,234 and, describe essential oil or essential oil components as regulators to improve drug bioavailability. However, no correlation or connection between the improvement of drug bioavailability and the inhibition of CYP, particularly CYP3A, is provided. Also, U.S. Pat. No. 6,063,809 correlates citrus-derived substances (such as grapefruit juice) to drug bioavailability due to anti-first-pass effect regulated by cytochrome P450.

There are also some publications which connect the improvement of drug bioavailability to inhibition of CYP3A activity. For examples, U.S. Pat. No. 5,962,522 describes the improvement of drug bioavailability by propyl gallate, which inhibits CYP3A enzymatic activities; U.S. Pat. No. 6,004,927 discloses certain naphthalenes and flavonoids, which reduce CYP3A drug biotransformation in the gut by acting either as an inhibitor of CYP3A activity or as a substrate of CYP3A activity; U.S. Pat. No. 6,028,054 discloses certain compounds, including flavonoids, inhibit CYP3A; and, Sarkar, *Cancer Chemother. Pharmacol.*, (1995), 36: 448–450, discloses that quercetin inhibits CYP3A isozymes.

In addition, there are reports relating to the regulation of CYP3A. For example, Hukkanen et al., *Am. J. Respir. Cell.*

Mol. Biol. (2000), 22: 360–6, disclose the induction of CYP3A5 by dexamethasone and phenobarbital in human alveolar type II cell-derived A549 adenocarcinoma cell line and by glucocorticoid in human lung cells.

Finally, there have been reports that certain chemical compounds can induce CYP3A expression or activity. For example, Backlund et al., *J. Biol. Chem.* (1997), 272: 31755–63, disclose that omeprazole increases CYP3A expression in rat hepatoma H4IIE cell line; Paolini et al., *Cancer Lett.* (1999), 145: 35–42, disclose that glycyrrhizin induces CYP3A in Sprague-Dawley rat liver monooxygenase; Paolini et al., *Life Sci.* (1998), 62: 571–82, disclose the induction of hepatic CYP3A in murine liver by glycyrrizin; Ronis et al., *Biochem. Pharmacol.* (1994), 48: 1953–65, disclose that clotrimazole induces CYP3A isozyme expression in male Sprague-Dawley rat and the male bobwhite quail; Backman et al., *Clin. Pharmacol. Ther.* (2000), 67: 382–90, disclose that tangeretin, a flavonoid, stimulates the catalytic activity of CYP3A4 in human liver microsomes.

In the invention to be presented in the following sections, various CYP3A inhibitors and enhancers are tested. These inhibitors and enhancers are natural compounds extracted from herbs which shows no sign of toxic effects. The CYP3A inhibitors inhibit the CYP3A enzymatic activity so as to improve the bioavailability of certain drugs in vivo. The CYP3A enhancers induce the CYP3A enzymatic activity so as to improve drug biotransformation by CYP3A, resulting in removal of active drugs. Thus, CYP3A inhibitors can be used as anti-first-pass effect compounds to improve the bioavailability of certain drugs or as chemopreventors by preventing the conversion of compounds into carcinogen caused by CYP3A. In addition, CYP3A enhancers can be used to improve biotransformation and elimination of active drugs or CYP3A substrates.

SUMMARY OF THE INVENTION

The present invention provides cytochrome P450 3A (CYP3A) inhibitors which are free bases or pharmacologically acceptable salts of at least one of the following compounds: α-naphthoflavone, β-naphthoflavone, apigenin, baicalein, β-myrcene, catechin, 3-phenylpropyl acetate, formononetin, gallic acid, hesperetin, hesperidin, isoquercitrin, lauryl alcohol, luteolin, luteolin-7-glycoside, narigin, nordihydroguaiaretic acid, quercitrin, swertiamarin, terpineol, and trans-cinnamaldehyde. The preferred CYP3A inhibitors are nordihydroguaiaretic acid, (+)-catechin, lauryl alcohol, gallic acid, hesperetin, hesperidin, trans-cinnamaldehyde, β-myrcene, and narigin. The most favorable CYP3A inhibitors are hesperidin, trans-cinnamaldehyde, and β-myrcene. These inhibitors are the inhibitors of various CYP3A isoforms, particularly CYP3A 4/5.

The above mentioned CYP3A inhibitors can be used as anti-first-pass effect compounds to improve the bioavailability of certain drugs, preferably erythromycin, felodipine, troleandomycin, nifedipine, cyclosporin, FK506, teffenadine, tamoxifen, lidocaine, triazolam, dapsone, diltiazem, lovastatin, simvastatin, quinidine, ethylestradiol, testosterone, midazolam, and alfentanil. These drugs are known to have low bioavailability when administered to patients.

The CYP3A inhibitors of the present invention are preferably orally administered to patients. The CYP3A inhibitors are preferably administered to patients via food or in an oral dosage form such as tablets or granules (which can be packaged in capsules). When the CYP3A inhibitors are administered to patients in the oral dosage form, optionally, at least one of the pharmaceutically acceptable excipients (such as a diluent, a filler, a binder, a disintegrant, a lubricant) is added to the tablets or capsules.

The CYP3A inhibitors can also be co-administered, preferably orally, with a drug to specifically improve the bioavailability of that drug. The examples of drugs that can be co-administered with the CYP3A inhibitors include erythromycin, felodipine, troleandomycin, nifedipine, cyclosporin, FK506, teffenadine, tamoxifen, lidocaine, triazolam, dapsone, diltiazem, lovastatin, simvastatin, quinidine, ethylestradiol, testosterone, midazolam, and alfentanil. The preferred drugs are erythromycin, nifedipine, cyclosporin, triazolam, lovastatin, simvastatin, and midazolam.

In addition, the CYP3A inhibitors can be used as chemopreventors to prevent biotransformation of procarcinogenic compounds or substances to carcinogens via CYP3A enzymatic activity. They can also orally administer to patent with cancer to improve the bioavailability of cancer drug or reduce CYP3A enzymatic activity. Examples of cancer that can be treated by CYP3A inhibitors include intestinal or hepatic cancer, such as adenocarcinoma (intestinal cancer) and hepatoma (liver cancer).

The present invention also provides cytochrome P450 3A (CYP3A) enhancers. Examples of CYP3A enhancers include free bases or pharmacologically acceptable salts of at least one of the following compounds: apigenin, formononetin, and luteolin-7-glycoside. The CYP3A enhancers can be used to induce the biotransformation and degradation of drugs and improve the enzymatic activity of CYP3A in patients with hepatic failure which causes impairment of hepatic clearance, such as hepatitis or cirrhosis.

Figure 1:
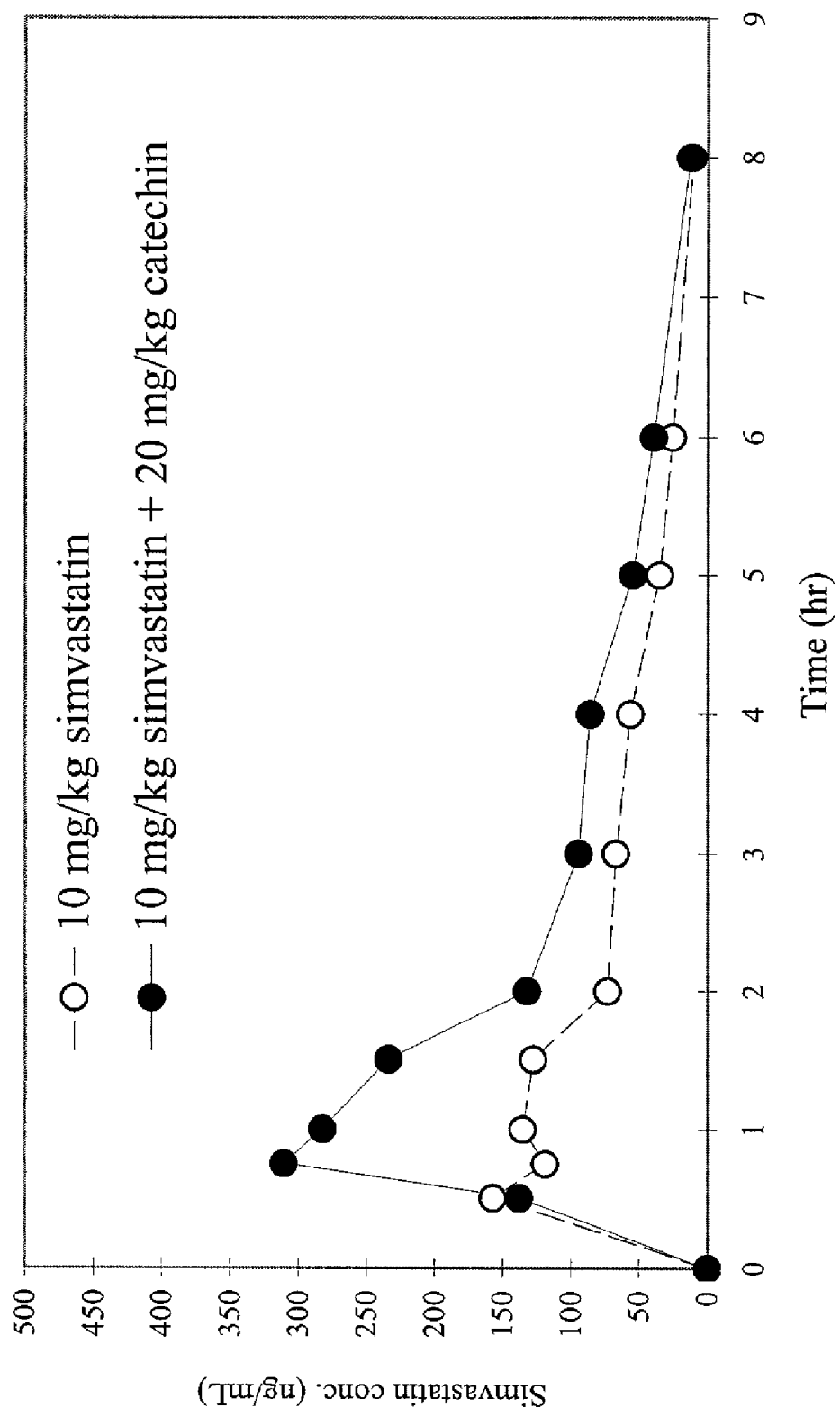
FIG. 1 shows a time course of the concentration of simvastatin in plasma of beagles ("Beagle 1 Experiment") after orally administered with 10 mg/kg of simvastatin (○) or 10 mg/kg of simvastatin together with 20 mg/kg of catechin (●).

DETAILED DESCRIPTION OF THE INVENTION.

Bioavailability of a drug (pharmaceutical composition) following oral dosing is a critical pharmacokinetic determinant, which can be approximated by the following formula:

$$F_{oral} = F_{Abs} \times F_G \times F_H$$

wherein $F_{oral}$ is the fraction of the oral dose that reaches the circulation in an active, unchanged form. $F_{Abs}$ is the fraction of the oral dose that is absorbed. $F_G$ is the fraction of the absorbed dose that successfully reaches the blood side of the gastrointestinal tract (GI). $F_H$ is the fraction of the drug in the GI blood supply that reaches the heart side of the liver. See e.g., U.S. Pat. No. 6,004,927, which is herein incorporated by reference.

Normally, an oral drug composition, from the time it is ingested till it is eliminated from the body (i.e., pharmacokinetics of the drug), follows the sequence of events which includes absorption through the various mucosal surfaces, distribution via the blood stream to various tissues, transformation in the liver and other tissues, action at the target site, and elimination of drug or metabolites in urine or bile. However, due to the following reasons: (1) that the drug is not absorbed through the GI tract and eliminated in the feces; (2) drug is biotransformed by the cells of the intestine to an inactive metabolite; or (3) the drug is eliminated by the cells of the liver, either by biotransformation and/or by transport into the bile, only a fraction of the oral drug dose can be utilized by the body.

The liver affects drug bioavailability. All blood from the gastronintestinal tract passes through the liver before going elsewhere in the body in all mammals, including humans. Due to its location, liver transformation of orally dosed drugs has a substantial "first-pass effect" on drug bioavailability that was thought to exceed effects in the gut. *Clin. Pharmacokinetics* (1993), 25:300–328.

Elimination of active drug by the liver occurs by one or both of two general pathways, namely biotransformation of the drug and excereotion of the drug into the bile. Biotransformation reactions have been classified into two broadly defined phases. Phases I biotransformation often utilizes reactions catalyzed by the cytochrome 450 enzymes, which are manifold and active in the liver and transform many chemically diverse drugs. A second biotransformation phase can add a hydrophilic group, such as glutathione, glucuronic acid or sulfate, to increase water solubility and speed elimination through the kidneys.

The present invention provides inhibitors for CYP3A enzymatic activity, which include free bases or pharmacologically acceptable salts of at least one of the following compounds: α-naphthoflavone, β-naphthoflavone, apigenin, baicalein, β-myrcene, catechin, 3-phenylpropyl acetate, formononetin, gallic acid, hesperetin, hesperidin, isoquercitrin, lauryl alcohol, luteolin, luteolin-7-glycoside, narigin, nordihydroguaiaretic acid, quercitrin, swertiamarin, terpineol, and trans-cinnamaldehyde. The inhibitory effects of these compounds are illustrated in Table 1.

The preferred CYP3A inhibitors are hesperidin, trans-cinnamaldehyde, and β-myrcene (Table 1). Among the preferred CYP3A inhibitors, trans-cinnamaldehyde is the most favorable one. The CYP3A inhibitors of the present invention is more effective against CYP3A4/5.

The CYP3A inhibitors are anti-first-pass effect compounds for particularly orally administered drugs. The "first-pass effect" of drugs given orally refers to the process of drug degradation during a drug's transition from initial ingestion to circulation in the blood stream. The word "drug" as used herein is defined as a chemical capable of administration to an organism, which modifies or alters the organism's physiology. More preferably, the word "drug" as used herein is defined as any substance intended for use in the treatment or prevention of disease, particularly for humans. Drug includes synthetic and naturally occurring pharmaceuticals, such as those listed in Merck Index, Merck Research laboratories, Whitehouse Station, N.J.; "The Physician's Desk Reference"; "Goodman and Gilman's The Pharmacological Basis of Therapeutics"; and "The united States Pharmacopoeia, The National Formulary". The compounds of these references are herein incorporated by reference. The word "drug" also includes compounds that have the indicated properties that are not yet discovered or available in the United States, and are pro-active, activated and metabolized forms of drugs.

The particular types of drugs which can be benefited from oral administration or co-administration of the CYP3A inhibitors include, but are not limited to, erythromycin, felodipine, troleandomycin, nifedipine, cyclosporin, FK506, teffenadine, tamoxifen, lidocaine, triazolam, dapsone, diltiazem, lovastatin, simvastatin, quinidine, ethylestradiol, testosterone, midazolam, and alfentanil. These drugs share the common characteristics of having low bioavailability rate in the body so that only a very small portion of the active ingredient of the drug can be used in the body.

It is not uncommon for a drug that is administered to a patient orally to be given in a 5-fold or greater amount than ultimately necessary due to the degradation that occurs in the patient's body after intake. For example, in the case of the antihistamine terfenadine, 99.5% of the active ingredient ferfenadine, when given by mouth, is quickly changed to metabolites, so that the bioavailability of terfenadine is approximately 0.5%. Also, cyclosporin A, which is often administered to organ transplant patients, has a median oral bioavailability of approximately 30% and a bioavailability range of approximately 8–92% among patients (U.S. Pat. No. 6,063,809).

Although the agent(s), enzyme type(s), biological processes, etc., which are responsible for the first-pass effect have not been fully identified, research has focused on agents capable of inhibiting the cytochrmoe P450 system. Inhibition of the P450 system is a model for in vitro determination of in vivo bioavailability enhancement. See, e.g., U.S. Pat. No. 5,478,723, which is incorporated herein by reference. Based on the information provided by this patent, the in vivo bioavailability of a drug can be determined by in vitro analysis of cytochrome P450 enzyme activity, such as by detecting the CYP3A activity in microsomes isolated from the liver.

CYP3A inhibitors of the present invention can be used as chemopreventors for prevention of cancer and for treatment of cancer. CYP3A is known to be the key xenobiotic-metabolizing (including detoxification and/or converting procarcinogens into carcinogens) enzymes in liver, lung, and intestine. Natural compounds which elevate the detoxification or decrease the carcinogenesis functions of CYP3A are known to be used to protect against cancer. (Siess et al., *Cancer lett.* (1997), 9:120:195–201). For example, natural products which can prevent CYP3A's activity to metabolized alfa toxin $B_1$ and alfa toxin $G_1$ into carcinogen, are known to serve as chempreventors for cancer.

Since the present CYP3A inhibitors inhibit the hepatic CYP3A activity (see Table 1), they can be used as either chemopreventors or compounds for treating patients with cancer, particularly hepatic or intestinal cancer.

CYP3A inhibitors of the present invention can be used, alone or co-administered with a drug, to improve the bioavailability of the drug. The CYP3A inhibitors can be provided in food or administered in the dosage form of tablets or granules (which can be further packaged into capsules). Conventional methods for making tablets or granules can be used. Additionally, excipients, such as microcrystalline cellulose (Avicel PH101® and Avicel PH102®), polyvinylpyrrolidone (Kollidon®, Plasdone®), corn starch, modified starches, gums, gelatinized starches (Sta Rx®) or modified starches such as sodium starch glycolate (Primojel®), sugar, polyethylene glycol, polyvinylpyrroline, polyvinyl alcohol, hydroxypropyl cellulose, methylcellulose, hydroxymethyl cellulose, hydroxypropyl methylcellulose, polyvinyl acetal diethylaminoacetate, are commonly used.

For drugs which are intended to be used in duodenum and intestine, additional excipients which are to be used as enteric coating materials, can be used. These include cellulose acetate phthalate, hydroxypropyl methylcellulose phthalate, polyvinyl acetate phthalate, carboxymethylethylcellulose, co-polymerized methacrylic acid/methacrylic acid methyl esters such as Eudragit® (Röhm Pharma), Aquateric® (FMC Corporation), Coating CE 5142 (BASF). In the case of tablets, plasticizers, colorants, pigments, titanium oxide, talc and other additives may also be included.

The present invention also provides enhancers of CYP3A. Examples of the CYP3A enhancers are listed in Table 2, which included, but were not limited to, free bases or the pharmacologically acceptable salts of formononetin, luteolin-7-glycoside and apigenin. The CYP3A enhancers of the present invention can be used along with other drug to decrease the bioavailability of the other drug, or used alone to induce the enzymatic activity of CYP3A, particularly in liver and intestine.

The following examples are illustrative, and should not be viewed as limiting the scope of the present invention. Reasonable variations, such as those occur to reasonable artisan, can be made herein without departing from the scope of the present invention.

In particular, in Example 3 of the present invention, an in vivo study showing the effect of oral administration of one of the CYP3A inhibitor, (+)-catechin, on the increase of bioavailability of one of the orally administered first-pass effect drugs, simvastatin, in beagles was conducted. Similar results were obtained using other CYP3A inhibitors described in the present invention with other first-pass effect drugs. Example 3 is not to be construed as limiting to only co-administration of (+)-catechin with simvastatin.

EXAMPLE 1

Preparation of Liver Homogenate

Rat liver microsomes were prepared according to the following steps:
1. A rat was sacrificed by decapitation.
2. Liver tissue was quickly excised from the sacrificed rat, and immediately moved into ice-cold 0.25 M sucrose solution for cooling; liver tissue was further washed to remove excess blood off the tissue.
3. The washed liver tissue was blotted dried and weighed.
4. More 0.25 M sucrose solution was added to the solution containing liver tissue to make up to four times of the weight of the starting solution, i.e., a 20% w/v liver homogenate.
5. The liver tissue was finely cut on ice until the homogenate contained no visible big fragments. Excess bubbles should be avoid during the cutting process.

EXAMPLE 2

Determination of CYP3A Activity By Erythromycin Demethylation Method

To measure the efficiency of CYP3A activity inhibitors and enhancers of the present invention, the following method was developed:

The tissue homogenate prepared according to Example 1 was mixed with 360 μl 1.15% potassium chloride (KCl) solution. Then, the following solutions were added orderly into the homogenate: 375 μl shotgun buffer, 50 μl cofactor, 40 μl 6 mM erythromycin, 50 μl 10 unit/ml G6PDH, 125 μl 90% microsome, 125 μl KHPO$_4$, 125 μl CYP3A activity inhibitor of the present invention.

The mixture solution was shaken at 37° C. for fifteen (15) minutes. One milliliter ZnSO$_4$, Ba(OH)$_2$ solution was added into the mixture solution and the solution was shaken to dissolve properly. The mixture was centrifuged for ten (10) minutes at 15,000 rpm. The supernatant 1 ml was removed from the mixture, and 0.6 ml Nash's Reagent solution was added into the mixture. The mixture was stored at 60° C. for ten (10) minutes. At the end, the mixture was cooled down to room temperature and a light absorbance at 412 nm was determined.

The results were shown in the following Tables 1 and 2.

TABLE 1

Inhibition of CYP3A Activity.

| CYP3A Activity Inhibitors | Concentration (mM) | CYP3A Activity (percentage of control) |
|---|---|---|
| Nordihydroguaiaretic Acid | 3.09 | 8.96 ± 1.79 |
| | 0.4 | 42.53 ± 0.49 |
| | 0.04 | 60.28 ± 1.95 |
| | 0.004 | 71.26 ± 1.95 |
| α-terpineol | 501.93 | 9.29 ± 1.07 |
| (+)-epicatechin | 0.45 | 14.66 ± 7.66 |
| | 1.41 | 23.29 ± 5.28 |
| | 1.55 | 27.96 ± 5.07 |
| Lauryl alcohol | 739.88 | 18.58 ± 1.46 |
| Trans-cinnamaldehyde | 10.22 | 30.95 ± 1.03 |
| Luteolin | 1.56 | 36.32 ± 1.26 |
| | 0.4 | 106.51 ± 8.16 |
| | 0.04 | 94.10 ± 10.37 |
| | 0.004 | 88.22 ± 0.00 |
| β-Naphthoflavone | 0.87 | 42.41 ± 4.08 |
| α-Naphthoflavone | 1.24 | 43.52 ± 2.93 |
| Glycyrrhizin | 0.269 | 42.96 ± 3.75 |
| Gallic acid | 77.07 | 44.09 ± 4.39 |
| | 24.66 | 43.65 ± 0.57 |
| | 4.3 | 43.86 ± 4.45 |
| Oleanolic acid | 77.07 | 44.64 ± 7.92 |
| | 0.522 | 55.95 ± 4.45 |
| Luteolin-7-glycoside | 0.04 | 98.71 ± 19.74 |
| | 0.0078 | 46.68 ± 0.17 |
| Nariagenin | 1.55 | 47.07 ± 9.87 |
| | 0.4 | 60.54 ± 15.51 |
| | 0.04 | 62.37 ± 12.33 |
| | 0.004 | 81.63 ± 5.21 |
| Narigin | 21.67 | 56.22 ± 22.87 |
| β-myrcene | 4.3 | 55.95 ± 4.45 |
| apigenin | 0.1 | 59.94 ± 2.50 |
| | 0.04 | 54.64 ± 5.16 |
| | 0.004 | 52.96 ± 1.15 |
| formononetin | 0.1 | 70.37 ± 5.79 |
| | 0.04 | 92.06 ± 0.77 |
| | 0.004 | 78.78 ± 2.76 |
| kaempferol | 0.4 | 80.11 ± 8.11 |
| | 0.04 | 76.57 ± 3.83 |
| | 0.004 | 73.03 ± 2.30 |
| isoquercitrin | 0.2 | 51.46 ± 6.68 |
| | 0.04 | 66.83 ± 5.03 |
| | 0.004 | 64.62 ± 1.53 |
| ergosterol | 0.4 | 59.57 ± 5.41 |
| | 0.04 | 63.71 ± 11.57 |
| | 0.004 | 64.59 ± 3.34 |
| (+)-catechin | 0.4 | 45.42 ± 6.13 |
| | 0.04 | 62.70 ± 8.53 |
| | 0.004 | 59.31 ± 2.94 |
| 3-phenylpropyl acetate | 0.4 | 53.89 ± 4.43 |
| | 0.04 | 70.50 ± 0.59 |
| | 0.004 | 60.33 ± 2.18 |
| umbelliferone | 16.96 | 90.33 ± 1.63 |
| | 5.43 | 98.85 ± 14.19 |
| | 1.84 | 76.22 ± 2.73 |
| | 0.4 | 90.00 ± 4.20 |
| | 0.04 | 84.87 ± 6.93 |
| | 0.004 | 89.00 ± 12.02 |
| hesperetin | 0.4 | 48.25 ± 4.62 |
| | 0.04 | 75.89 ± 3.31 |
| | 0.004 | 84.66 ± 3.04 |
| baicalein | 0.1 | 64.47 ± 4.75 |
| | 0.04 | 81.59 ± 4.76 |
| | 0.004 | 84.66 ± 3.04 |

TABLE 1-continued

Inhibition of CYP3A Activity.

| CYP3A Activity Inhibitors | Concentration (mM) | CYP3A Activity (percentage of control) |
|---|---|---|
| quercitrin | 0.4 | 98.67 ± 7.51 |
| | 0.04 | 73.56 ± 5.96 |
| | 0.004 | 55.06 ± 5.34 |
| quercetin | 0.4 | 91.62 ± 0.76 |
| | 0.04 | 77.52 ± 15.98 |
| | 0.004 | 75.76 ± 7.97 |
| swertiamarin | 0.4 | 65.63 ± 1.29 |
| | 0.04 | 67.88 ± 0.49 |
| | 0.004 | 79.71 ± 1.76 |
| hesperidin | 0.4 | 80.75 ± 4.18 |
| | 0.04 | 103.79 ± 6.37 |
| | 0.004 | 24.05 ± 5.06 |

TABLE 2

Enhancement of CYP3A Activity.

| CYP3A Activity Enhancers | Concentration (mM) | CYP3A Activity (percentage of control) |
|---|---|---|
| apigenin | 0.22 | 108.62 ± 1.28 |
| kaempferol | 1.46 | 111.35 ± 27.88 |
| formononetin | 0.123 | 113.74 ± 8.87 |
| luteolin-7-glycoside | 0.1 | 113.09 ± 5.99 |
| | 0.004 | 122.89 ± 40.06 |

The data shown in Tables 1 and 2 are the mean value of at least 3 experiments. The compounds listed in Table 1 demonstrated inhibitory effects on rat liver CYP3A. Among these compounds, nordihydroguaiaretic acid, (+)-catechin, lauryl alcohol, gallic acid, hesperetin, hesperidin, trans-cinnamaldehyde, β-myrcene, and narigin were particularly effective.

The compounds in Table 2 demonstrated enhancing effects on rat hepatic CYP3A. Among these compounds, formononetin, luteolin-7-glycoside and apigenin were particularly effective.

The chemical compounds as shown in Tables 1 and 2 were commercially available and could be separated from natural herbs.

EXAMPLE 3

Effect of Catechin on Plasma Concentration of Simvastatin in Beagles

Purpose:

The purpose of this study is to determine the effects of orally administered CYP3A inhibitor(s) on the bioavailability of various first-pass-effect compounds in beagles. The CYP3A inhibitor used in this study is catechin. The first-pass-effect compound tested in this study is simvastatin.

Catechin is 2R-trans-2-(3,4-dihydroxyphenyl)-3,4-dihydro-2H-1-benopyran-3,5,7-triol. Catechins, also known as flavonoids, represent a group of naturally existed compounds obtainable by extraction from plants containing them. Such plants and the catechins they contain are well known to those skilled in the art, such as *Catechu gambir* (Uncaria family) and green tea (*Camellia sinensis*). The catechins may be extracted from either a single plant or any mixture of plants containing them. Examples of the most common catechins which are obtained by extraction from these plants are, catechin, epicatechin, gallocatechin, epigallocatechin, epicatechingallate and epigallocatechingallate. Catechin is preferably used in combination with one of the other catechins mentioned above.

Simvastatin is a hexahydronaphthalene derivative which is well known as being a potent inhibitor of the enzyme HMG-CoA reductase, the rate-controlling enzyme in the biosynthetic pathway for formation of cholesterol in the human body. See U.S. Pat. No. 4,444,784. Simvastatin is widely used in hyperchotesterolaemic treatments. Simvastatin is currently sold under the tradename of Zocor® by Merck.

Both catechin and simvastatin were orally administered at the same time into beagles. The plasma concentration of simvastatin was monitored in the animals as described in the method:

Method:

Two groups of beagles were used in this study. In the first group, each beagle was given 10 mg/kg of simvastatin together with 20 mg/kg of catechin orally, both dissolved in polyethylene glycol (PEG400) solution (the "simvastatin+catechin" group). In the second group, 10 mg/kg of simvastatin in PEG400 solution (the "simvastatin" group).

Blood samples were taken from the forearm vein of the animals at 0.5, 0.75, 1, 1.5, 2, 3, 4, 5, 6, and 8 hours after the oral administration. The blood samples were analyzed by high performance liquid chromatography (HPLC) to determine the pharmacokinetics (including the half-life and area under the plasma concentration curve of simvastatin) in vivo.

Figure 2:
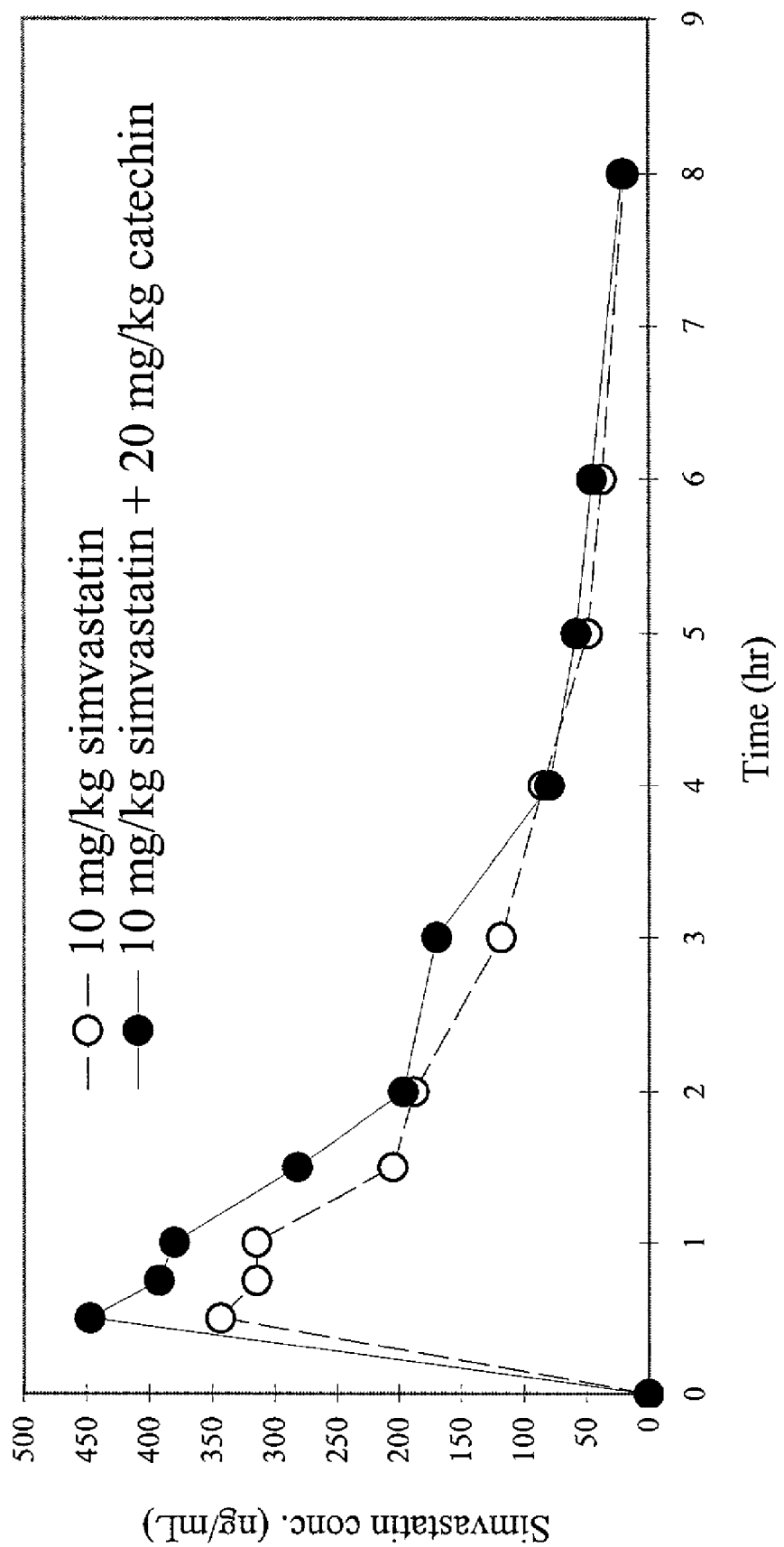
FIG. 2 shows shows a time course of the concentration of simvastatin in plasma of beagles ("Beagle 2 Experiment") after orally administered with 10 mg/kg of simvastatin (○) or 10 mg/kg of simvastatin together with 20 mg/kg of catechin (●).

Result:

As shown in FIGS. 1 and 2, the plasma concentration of simvastatin in the "simvastatin+catechin" and "simvastatin" groups peaked less than 0.75 hours after oral administration of the pharmaceutical compositions. Both groups demonstrated about the same elimination half-life of simvastatin after the oral uptake of simvastatin. However, the concentrations of simvastatin in the "simvastatin+catechin" group were much higher than the "simvastatin" group.

Table 1 shows the results of the pharmacokinetic studies of the two pharmaceutical compositions.

As shown in Table 1, the extend of absorption of simvastatin, as determined by AUC (area under curve), shows that the "simvastatin+catechin" group is far much better than the "simvastatin" group (Beagle 1: 785 [simvastatin+catechin Group] vs. 492 [simvastatin Group]; Beagle 2: 1154 [simvastatin+catechin Group] vs. 949 [simvastatin Group]).

The results of FIGS. 1, 2 and Table 1 show that the addition of catechin to simvastatin greatly improves the absorption and bioavailability of simvastatin in beagles (as comparing the simvastatin Group).

TABLE 1

Simvastatin pharmacokinetic parameters of beagles after oral administration of 10 mg/kg simvastatin with or without 20 mg/kg of catechin

| | Beagle 1 | | Beagle 2 | |
|---|---|---|---|---|
| Parameters | With Catechin | Without Catechin | With Catechin | Without Catechin |
| Total AUC (hr*ng/mL) | 785 | 492 | 1154 | 949 |
| Tmax (hr) | 0.75 | 0.50 | 0.50 | 0.50 |
| Cmax (ng/mL) | 311 | 157 | 447 | 343 |

TABLE 1-continued

Simvastatin pharmacokinetic parameters of beagles after oral administration of 10 mg/kg simvastatin with or without 20 mg/kg of catechin

| | Beagle 1 | | Beagle 2 | |
|---|---|---|---|---|
| Parameters | With Catechin | Without Catechin | With Catechin | Without Catechin |
| Elimination half life (hr) | 1.47 | 1.70 | 2.09 | 1.96 |
| MRT (hr) | 2.79 | 3.06 | 2.76 | 2.84 |

While the invention has been described by way of examples and in terms of the preferred embodiments, it is to be understood that the invention is not limited to the disclosed embodiments. On the contrary, it is intended to cover various modifications as would be apparent to those skilled in the art. Therefore, the scope of the appended claims should be accorded the broadest interpretation so as to encompass all such modifications.

We claim:

1. A method for inhibiting cytochrome P450 3A (CYP3A) enzymatic activity in a patient comprising: orally administering the CYP3A inhibitor swertiamarin to said patient in need thereof and, administering another drug that undergoes a first-pass effect selected from the group consisting of erythromycin, felodipine, troleandomycin, nifedipine, cyclosporine, FK506, terfenadine, tamoxifen, lidocaine, triazolam, dapsone, diltiazem, lovastatin, simvastatin, quinidine, ethyl estradiol, testosterone, midazolam and alfentanil; wherein said CYP3A inhibitor is a free base or pharmacologically acceptable salt.

2. The method according to claim 1, wherein said pharmaceutical composition is administered orally to said patient with food or in the form of a capsule or tablet.

3. The method according to claim 1, wherein said drug that undergoes a first-pass effect and said CYP3A inhibitor are co-administered orally.

4. The method according to claim 1, wherein wherein said drug that undergoes a first-pass effect is simvastatin.

* * * * *